United States Patent [19]

Malfer

[11] Patent Number: 5,122,616
[45] Date of Patent: Jun. 16, 1992

[54] SUCCINIMIDES

[75] Inventor: Dennis J. Malfer, Crestwood, Mo.

[73] Assignee: Ethyl Petroleum Additives, Inc., St. Louis, Mo.

[21] Appl. No.: 410,902

[22] Filed: Sep. 22, 1989

Related U.S. Application Data

[63] Continuation-in-part of Ser. No. 405,222, Sep. 11, 1989, Pat. No. 4,997,456.

[51] Int. Cl.$^5$ ............... C07D 207/452; C07D 403/12; C10L 1/18
[52] U.S. Cl. ............................ 548/546; 548/52 D; 44/347
[58] Field of Search ......................... 548/546

[56] References Cited

U.S. PATENT DOCUMENTS

| | | | |
|---|---|---|---|
| 3,037,051 | 5/1962 | Stromberg | 260/485 |
| 3,185,704 | 5/1965 | Kahn et al. | 260/326.3 |
| 3,806,456 | 4/1974 | Vogel | 252/51.5 |
| 3,847,561 | 11/1974 | Feldman | 44/62 |
| 3,882,128 | 5/1975 | McLaren et al. | 260/28.5 A |
| 3,897,351 | 7/1975 | Davis et al. | 252/34 |
| 4,098,585 | 7/1978 | Vartanian et al. | 44/64 |
| 4,198,306 | 4/1980 | Lewis | 252/51.5 |
| 4,203,730 | 5/1980 | Hanson | 44/71 |
| 4,240,803 | 12/1980 | Andress, Jr. | 44/63 |
| 4,329,249 | 5/1982 | Forsberg | 252/34.7 |
| 4,368,133 | 1/1983 | Forsberg | 252/75 |
| 4,435,297 | 3/1984 | Forsberg | 252/34.7 |
| 4,447,348 | 5/1984 | Forsberg | 252/75 |
| 4,448,703 | 5/1984 | Forsberg | 252/75 |
| 4,505,832 | 3/1985 | Whiteman et al. | 252/42.1 |
| 4,652,273 | 3/1987 | Maldonado et al. | 44/63 |
| 4,780,111 | 10/1988 | Dorer et al. | 44/63 |
| 4,863,487 | 9/1989 | Meyer et al. | 44/63 |
| 4,895,578 | 1/1990 | Meyer et al. | 44/63 |

FOREIGN PATENT DOCUMENTS

| | | |
|---|---|---|
| 20037 | 5/1980 | European Pat. Off. |
| 0074199 | 8/1982 | European Pat. Off. |
| 0331306 | 2/1989 | European Pat. Off. |
| 3814601 | 4/1987 | Fed. Rep. of Germany |
| 8303616 | 4/1982 | PCT Int'l Appl. |
| 8503504 | 1/1985 | PCT Int'l Appl. |
| 1111837 | 5/1968 | United Kingdom |

*Primary Examiner*—David B. Springer
*Attorney, Agent, or Firm*—John F. Sieberth; David E. LaRose; Doris M. Thompson

[57] ABSTRACT

Succinimides useful as detergents in fuels are prepared by reacting (a) at least one substituted succinic acid or acid derivative thereof containing an average of from 16 to about 50 carbon atoms in the molecule and having an acyclic aliphatic substituent group containing an average of at least 12 but less than 30 carbon atoms, with (b) at least one alkanol polyamine containing an average of at least 4 carbon atoms and containing at least one primary amino group.

35 Claims, No Drawings

SUCCINIMIDES

REFERENCE TO RELATED APPLICATION

This application is a continuation-in-part of application Ser. No. 405,222 (Case EI-5808) filed Sep. 11, 1989 now U.S. Pat. No. 4,997,456.

TECHNICAL FIELD

This invention relates to detergents for internal combustion engines More particularly it relates to novel ashless dispersant-detergents capable of reducing and/or preventing the deposit of solid materials in internal combustion engines and in particular in the fuel intake systems and/or related engine parts.

BACKGROUND

The prior art discloses many ashless dispersants useful as additives in fuels and lubricant compositions. A large number of such ashless dispersants are derivatives of high molecular weight carboxylic acid acylating agents. Typically, the acylating agents are prepared by reacting an olefin (e.g., a polyalkene such as polybutene) or a derivative thereof, containing for example at least 30 to 50 aliphatic carbon atoms, with an unsaturated carboxylic acid or derivative thereof such as acrylic acid, methacrylic acid, maleic acid, fumaric acid and maleic anhydride. Dispersants are prepared from the high molecular weight carboxylic acid acylating agents by reaction with, for example, amines characterized by the presence within their structure of at least one N-H group, alcohols, reactive metal or reactive metal compounds, and combinations of the above. U.S. Pat. No. 4,234,435 summarizes some of the prior art relative to the preparation of such carboxylic acid derivatives.

It also has been suggested that the carboxylic acid derivative compositions such as those described above can be post-treated with various reagents to modify and improve the properties of the compositions. Acylated nitrogen compositions prepared by reacting the acylating reagents described above with an amine can be post-treated, for example, by contacting the acylated nitrogen compositions thus formed with one or more post-treated reagents selected from the group consisting of boron oxide, boron oxide hydrate, boron halides, boron acids, esters of boron acid, carbon disulfide, sulfur, sulfur chlorides, alkenyl cyanides, carboxylic acid acylating agents, aldehydes, ketones, phosphoric acid, epoxides, etc. Lists of the prior art relating to post-treatment of carboxylic ester and amine dispersants with reagents such as those described above are contained in a variety of patents such as U.S. Pat. Nos. 4,203,855 (Col. 19, lines 16-34) and 4,234,435 (Col. 42, lines 33-46).

U.S. Pat. No. 3,216,936 describes lubricant additives which are compositions derived from the acylating of alkylene polyamines. More specifically, the compositions are obtained by reaction of an alkylene amine with an acidic mixture consisting of a hydrocarbon-substituted succinic acid having at least about 50 aliphatic carbon atoms in the hydrocarbon group and an aliphatic monocarboxylic acid, and thereafter removing the water formed by the reaction. The ratio of equivalents of said succinic acid to the mono-carboxylic acid in the acidic mixture is from about 1:0.1 to about 1:1. The aliphatic mono-carboxylic acids contemplated for use include saturated and unsaturated acids such as acetic acid, dodecanoic acid, oleic acid, naphthenic acid, formic acid, etc. Acids having 12 or more aliphatic carbon atoms, particularly stearic acid and oleic acid, are especially useful. The products described in the '936 patent also are useful in oil-fuel mixtures for two-cycle internal combustion engines British Pat. No. 1,162,436 describes ashless dispersants useful in lubricating compositions and fuels. The compositions are prepared by reacting certain specified alkenyl substituted succinimides or succinic amides with a hydrocarbon-substituted succinic acid or anhydride. The arithmetic mean of the chain lengths of the two hydrocarbon substituents is greater than 50 carbon atoms. Formamides of monoalkenyl succinimides are described in U.S. Pat. No. 3,185,704. The formamides are reported to be useful as additives in lubricating oils and fuels.

U.S. Pat. Nos. 3,639,242 and 3,708,522 describe compositions prepared by post-treating mono- and polycarboxylic acid esters with mono- or polycarboxylic acid acylating agents. The compositions thus obtained are reported to be useful as dispersants in lubricants and fuels.

U.S. Pat No. 4,780,111 describes fuel compositions containing a hydrocarbon-soluble dispersant prepared generally by the post-treatment of a nitrogen-containing composition with mono- and polycarboxylic acids which may be aliphatic or aromatic carboxylic acids, preferably the latter. The nitrogen-containing compositions which are post-treated in accordance with U.S. Pat. No. 4,780,111 are obtained by reacting an acylating agent with alkylene polyamines or alkanol amines. The patent reports that when such fuel compositions are utilized in internal combustion engines, and in particular, fuel-injected internal combustion engines, the amount of solid deposits on the various parts of the internal combustion engines are reduced.

Use of such post-treatment procedures adds to the complexity of the production process and to the cost of the product so formed.

THE INVENTION

This invention provides novel compositions of matter, more particularly novel additives useful as fuel detergents. Such compounds require no post-treatment procedures such as described for example in U.S. Pat. No. 4,780,111. Moreover, the fuel compositions containing such additives have been found highly effective in reducing or preventing carburetor or injector deposit formation or build up in internal combustion engines.

In accordance with one of its embodiments this invention provides a hydrocarbon-soluble succinimide prepared by reacting
  a) at least one substituted succinic acid or acid derivative thereof containing an average of from 16 to about 50 carbon atoms in the molecule and having an acyclic aliphatic substituent group containing an average of at least 12 (preferably at least 16) but less than 30 carbon atoms, with
  b) at least one alkanol polyamine containing an average of at least 4 carbon atoms and containing at least one primary amino group.

In another embodiment of this invention, the succinimide is formed from an alkanol polyamine with contains only one primary amino group in the molecule In still another embodiment of this invention, the alkanol polyamine used in forming the succinimide contains an average of more than one primary amino group in the molecule. In such case, the resultant succinimide may contain an average of one or less than one or more than one succinimide group per molecule. In yet another embodiment of this invention, the alkanol polyamine used in forming the succinimide contains an average of at least two primary amino groups in the molecule.

This invention involves, inter alia, the discovery that by acylating an alkanol polyamine with a relatively short-chain acylating agent, a highly effective detergent for use in fuels can be formed without need for post-treatment such as is referred to and described for example in U.S. Pat. No. 4,780,111. Hence production and fuel treating costs can be kept to a minimum. Moreover, because the resultant succinimide product has a relatively low molecular weight, its content of polar constituency can be relatively high on a weight basis. Thus a given quantity of a detergent of this invention can provide the same effectiveness in inhibiting deposit formation on critical engine parts such as carburetor nozzles and the like as a substantially larger quantity of a polyamine acylated with a long chain acylating agent of the type described heretofore. And the detergents of this invention have good fuel solubility, and exhibit little if any tendency to leave gums or residues in areas where the fuel is aspirated, as in the carburetor or in other similar parts of the fuel intake systems. This invention involves the further discovery that certain structural configurations in the short chain succinic acid or acid derivative thereof can provide acylated alkanol polyamine detergents of exceptional effectiveness in keeping certain fuel intake system parts essentially free of deposits.

Pursuant to one preferred embodiment of this invention the acylating agent used in making the above detergent is at least one substituted succinic acid or acid derivative thereof (anhydride, acyl halide or lower alkyl ester) containing an average of from 16 to about 50 carbon atoms in the molecule and having a substantially straight chain acyclic aliphatic substituent group (most preferably alkyl or alkenyl) containing an average of at least about 12 but less than 30, and preferably an average of at least 14 but no more than 28 carbon atoms.

In another preferred embodiment the acylating agent used in making the above detergent is at least one substituted succinic acid or acid derivative thereof containing an average of from 16 to about 50 carbon atoms in the molecule and having an acyclic aliphatic substituent group bifurcated on its beta carbon atom into two branches, one of which contains at least 4 carbon atoms and the other of which contains at least 6 carbon atoms, such substituent group containing an average of at least 12 but less than 30 carbon atoms.

Preferably, the alkanol polyamine used in forming the succimides with the preferred acylating agents referred to in the immediately preceding two paragraphs is one or a mixture of alkanol polyamines represented by the general formula

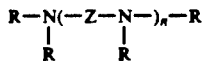

wherein Z is an alkylene group of from 2 to about 4 carbon atoms; each R is independently a hydrogen atom or an organic group which contains 1 to about 8 carbon atoms and is a hydrocarbyl, hydroxy-substituted hydrocarbyl, or primary amino-substituted hydrocarbyl group; and n is 1 to about 10; with the provisos that at least one R group is a hydroxy-substituted hydrocarbyl group, and that the compound contains at least one primary amino group. Use of 2-(2-aminoethylamino)ethanol is especially preferred.

In accordance with still another preferred embodiment, the detergent is a hydrocarbon-soluble substituted succinimide represented by the general formula

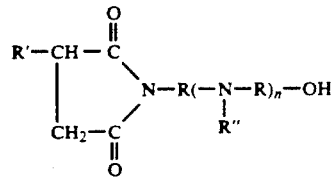

where R is alkylene of 2 to 4 carbon atoms, R' is a substantially straight chain alkyl or alkenyl group averaging at least 12 but less than 30 and preferably at least 14 but no more than 28 carbon atoms, R" is a hydrogen atom or alkyl of 1 to 5 carbon atoms, and n is an integer in the range of 1 to 10.

In yet another preferred embodiment the detergent of this invention is a substituted succinimide represented by the general formula

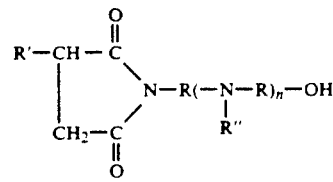

where R is alkylene of 2 to 4 carbon atoms, R' is an alkyl or alkenyl group bifurcated on its beta carbon atom into two branches one of which contains at least 4 carbon atoms and the other of which contains at least 6 carbon atoms, said group containing an average of at least 12 but less than 30 carbon atoms, R" is a hydrogen atom or alkyl of 1 to 5 carbon atoms, and n is an integer in the range of 1 to 10.

These and other embodiments, features and advantages of this invention will become still further apparent from the ensuing description and appended claims.

The compounds of this invention are especially useful as detergent additives for normally liquid hydrocarbon fuels in the gasoline boiling range, including hydrocarbon base fuels. The term "petroleum distillate fuel" also is used to describe the fuels which can be utilized in the fuel compositions of the present invention and which have the above characteristic boiling points. The term, however, is not intended to be restricted to straight-run distillate fractions. The distillate fuel can be straight-run distillate fuel, catalytically or thermally cracked (including hydrocracked) distillate fuel, or a mixture of straight-run distillate fuel, naphthas and the like with cracked distillate stocks. The hydrocarbon fuels also can contain non-hydrocarbonaceous materials such as alcohols, ethers, organo-nitro compounds, etc. Such materials can be mixed with the hydrocarbon fuel in varying amounts of up to about 10-20% or more. For example, alcohols such as methanol, ethanol, propanol and butanol, and mixtures of such alcohols are included in commercial fuels in amounts of up to about 10%. Other examples of materials which can be mixed with the fuels include diethyl ether, methyl ethyl ether, methyl tertiary butyl ether, and nitromethane. Also included within the scope of the invention are liquid fuels derived from vegetable or mineral sources such as corn, alfalfa, shale and coal. Also, the base fuels used in the formation of the fuel compositions of the present invention can be treated in accordance with well-known commercial methods, such as acid or caustic treatment, hydrogenation, solvent refining, clay treatment, etc.

Gasolines are supplied in a number of different grades depending on the type of service for which they are intended. The gasolines utilized in the present invention include those designed as motor and aviation gasolines. Motor gasolines include those defined by ASTM specification D-430-73 and are comprised of a mixture of olefins, paraffins, isoparaffins, naphthenes and occasionally diolefins. Motor gasolines normally have a boiling range within the limits of about 70° F. to 450° F. while aviation gasolines have narrower boiling ranges, usually within the limits of about 100° F.–330° F.

Fuel compositions containing a minor, property improving amount of at least one hydrocarbon-soluble detergent of the type described herein have the desirable ability of preventing or minimizing undesirable engine deposits, especially in the carburetor and fuel injector nozzles.

As noted above, the detergents for use in such hydrocarbon fuels are made from one or more aliphatic succinic acid acylating agents. As is well known, in reaction with co-reactive amines, such acylating agents may be used in the free acid form, in the form of a derivative thereof such as the anhydride, ester, acyl halide, or as a combination of any two or more of the foregoing.

Preferred acylating agents are alkyl and/or alkenyl succinic anhydrides in which the alkyl or alkenyl group is substantially straight chain in configuration and contains 12 to 26 carbon atoms, and even more preferably an average of about 18 to about 24 carbon atoms. An especially preferred acylating agent of this type is octadecenylsuccinic acid or anhydride.

Still another preferred acylating agent is an alkyl- or alkenylsuccinic acid or anhydride in which the alkyl or alkenyl group is bifurcated on the beta-carbon atom and is composed of two substantially linear chains. Preferred alkyl groups of this type may be represented by the formula

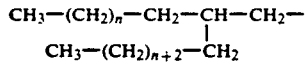

where n is an integer in the range of 2 to 10. A preferred group of such bifurcated alkenyl groups may be represented by the formula

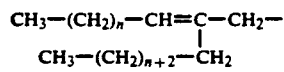

where n is an integer in the range of 2 to 10. It will be understood and appreciated that the double bond in such alkenyl group may be isomerized to different positions from that depicted (which is the preferred position) by treating the alkenylsuccinic acid or anhydride with an isomerization catalyst such as silica gel, a trialkylborane, or the like. Such alkyl- and alkenyl-substituted succinic acids and anhydrides can be formed from dimerized 1-olefins such as by dimerizing 1-hexene, 1-heptene, 1-octene, 1-nonene, 1-decene, 1-undecene, 1-dodecene, 1-tetradecene, 4-methyl-1-pentene, 6-methyl-1-heptene, 5-ethyl-1-decene, or 3,5,5-trimethyl-1-undecene with an aluminum alkyl dimerization catalyst according to known procedures. See for example Ziegler et al, *Ann.* 629, 121–166 (1960) all disclosure of which is incorporated herein by reference. The resultant dimerized olefin (sometimes referred to as a vinylidene olefin) is then used to alkylate maleic anhydride or an ester of maleic acid, etc., to form the alkenyl-substituted succinic acid compound by the "ene" reaction. See in this connection Hoffman, *Angew. Chem., Int. Ed.* (English), 8, 556–577 (1969); Snider, *J. Org. Chem.*, 39, 255 (1974); and Keung et al, *J. Chem. Educ.*, 49, 97–100 (1972), all disclosures of which are incorporated herein by reference. As is well known, the "ene" reaction may be facilitated by the use of a catalyst such as aluminum trichloride, alkyl aluminum sesquichloride or the like. To form the bifurcated alkyl substituent, the bifurcated alkenyl group of the resultant alkenyl-substituted succinic acid compound may be hydrogenated to saturate the double bond.

Similarly suitable alkyl- or alkenylsuccinic acids or anhydrides in which the alkyl or alkenyl group is bifurcated on the beta-carbon atom into two branches can be formed in analogous fashion using co-dimerized 1-olefin such as by co-dimerizing 1-butene and 1-octene, 1-hexene and 1-decene, 1-pentene and 1-dodecene, 4-methyl-1-pentene and 1-tetradecene, 1-octene and 1-decene, 1-nonene and 1-decene, 1-decene and 1-dodecene, 1-dodecene and 1-tetradecene, 2,7-dimethyl-1-octene and 1-decene, 2,7-dimethyl-1-octene and 1-dodecene, 1-tetradecene and 1-pentadecene, etc., using a co-dimerization catalyst such as an aluminum alkyl. Such co-dimerized olefins are then used in the "ene" reaction in the same manner as described above. Hydrogenation of the alkenyl succinic acid compound (anhydride, ester, etc.) yields the corresponding bifurcated alkyl succinic acid compound.

The acylating agent may contain polar substituents provided that the polar substituents are not present in proportions sufficiently large to alter significantly the hydrocarbon character of the acylating agent. Typical suitable polar substituents include halo, such as chloro and bromo, oxo, oxy, formyl, sulfenyl, sulfinyl, thio, nitro, etc. Such polar substituents, if present, preferably do not exceed 10% by weight of the total weight of the hydrocarbon portion of the acylating agent, exclusive of the carboxyl groups.

Reference may be had, for example to U.S. Pat. Nos. 3,087,936; 3,163,603; 3,172,892; 3,219,666; 3,272,746; 3,306,907; 3,346,354; and 4,234,435 for synthesis procedures which may be used, or modified for use, in preparing the hydrocarbon-substituted succinic acid-type acylating agents with the proviso of course that the materials used result in the production of an acylating agent containing an average of up to about 50 carbon atoms and having an acyclic aliphatic group of at least about 12 but less than 30 carbon atoms. In the interest of brevity, these patents are incorporated herein for their disclosure of suitable synthesis procedures which may be adapted for use in producing such succinic acid-type acylating agents.

As disclosed in the foregoing patents, there are several processes for preparing the acids. As utilized in this invention, the process involves the reaction of (1) maleic acid, or an acid derivative thereof, e.g., the acid halide, or anhydride with (2) an ethylenically unsaturated hydrocarbon containing at least about 12 but less than 30 aliphatic carbon atoms or a chlorinated hydrocarbon containing at least about 12 but less than 30 aliphatic carbon atoms at a temperature within the range of about 100°-300° C. The chlorinated hydrocarbon or ethylenically unsaturated hydrocarbon reactant can, of course, contain polar substituents, short chain (e.g., methyl, ethyl, etc.) pendant groups, and additional non-conjugated unsaturation. It is these hydrocarbon reactants which provide most of the aliphatic carbon atoms present in the acyl moiety of the final products.

When preparing the substituted succinic acid acylating agent according to one of these two processes, the maleic acid reactant usually corresponds to the formula $R'(-COOH)_n$, where $R'$ is characterized by the presence of an ethylenically unsaturated carbon-to-carbon covalent bond and n is the integer 2. The acidic reactant can also be the corresponding carboxylic acid halide, anhydride, ester, or other equivalent acylating agent and mixtures of one or more of these. Ordinarily, the total number of carbon atoms in the maleic acid reactant will not exceed 10 and generally will not exceed 6. Exemplary acidic reactants are maleic acid, maleic anhydride, fumaric acid, methylmaleic acid, methylmaleic anhydride, ethylmaleic acid, ethylmaleic anhydride, propylmaleic anhydride, butylmaleic anhydride, chloromaleic acid, and the like. Due to considerations of economy and availability, the acid reactants usually employed are maleic acid and maleic anhydride.

The substantially saturated aliphatic hydrocarbon-substituted succinic acid and anhydrides are especially preferred as acylating agents used as starting materials in the present invention. The succinic acid acylating agents are readily prepared by reacting maleic anhydride with an olefin or a chlorinated hydrocarbon of suitable chain length such as a chlorinated polyolefin. The reaction involves merely heating the two reactants at a temperature of about 100°-300° C., preferably, 100°-200° C. The product from such a reaction is a substituted succinic anhydride where the substituent is derived from the olefin or chlorinated hydrocarbon as described in the above-cited patents. The product may be hydrogenated to remove all or a portion of any ethylenically unsaturated covalent linkages by standard hydrogenation procedure, if desired. The substituted succinic anhydrides may be hydrolyzed by treatment with water or steam to the corresponding acid and either the anhydride or the acid may be converted to the corresponding acid halide or ester by reacting with phosphorus halide, phenols, or alcohols.

The ethylenically unsaturated hydrocarbon reactant and the chlorinated hydrocarbon reactant used in the preparation of the acylating agents are principally olefins, olefin oligomers, substantially saturated petroleum fractions and substantially saturated olefin oligomers and the corresponding chlorinated products. They contain an average of from 12 to below about 30 carbon atoms in the molecule. The oligomers and chlorinated oligomers derived from mono-olefins having from 2 to about 4 carbon atoms are preferred. The especially useful oligomers are the oligomers of such 1-monoolefins as ethylene, propene, 1-butene, and isobutene. Oligomers of medial olefins, i.e., olefins in which the olefinic linkage is not at the terminal position, likewise are useful. These are exemplified by 2-butene.

The low molecular weight interoligomers of 1-monoolefins such as illustrated above with each other and with other inter-oligomerizable olefinic substances are also useful sources of the ethylenically unsaturated reactant. Such interoligomers contain an average from 12 to below about 30 carbon atoms in the molecule, and include for example, those prepared by oligomerizing ethylene with propene, ethylene with isobutene, and ethylene with 1-butene, etc.

The chlorinated hydrocarbons and chlorinated ethylenically unsaturated hydrocarbons used in the preparation of the acylating agents also contain an average of 12 to below about 30 carbon atoms in the molecule. The preferred reactants are the above-described olefins and chlorinated olefins containing an average of at least 16 carbon atoms, preferably about 16 to about 28 carbon atoms.

The other reactant used in the formation of the detergents of this invention is one or a mixture of alkanol polyamines containing in the molecule an average of at least 4 carbon atoms, for example an average in the range of 4 to about 50, and preferably from 4 to about 20 carbon atoms. Such compounds may be represented by the general formula

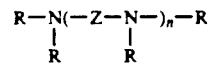

wherein Z is alkylene of from 1 to about carbon atoms (preferably from 2 to 4 carbon atoms); each R is independently a hydrogen atom, or (a) a hydrocarbyl group, or (b) a hydroxy-substituted hydrocarbyl group, or (c) a primary amino-substituted hydrocarbyl group, in which the groups of (a), (b), or (c) contain from 1 to about 8 carbon atoms (preferably from 2 to 4 carbon atoms); and n is 1 to about 10; with the proviso that at least one R group is a hydrogen atom such that the compound is co-reactive with the carboxylic acylating agent being employed therewith, and the proviso that at least one R group is a hydroxy-substituted hydrocarbyl group. Preferably the compound contains at least one primary amino group.

Preferably, n is an integer less than about 6, and the alkylene group (Z) is preferably a lower alkylene group such as dimethylene, trimethylene, tetramethylene, etc.

Examples of such alkanol polyamines include alkanol polyamines having at least one primary amino group in the molecule such as, for example, N-(2-hydroxyethyl)ethylene diamine (also known as 2-(2-aminoethylamino)ethanol), 2-(2-aminoethylamino)-1-methylethanol, 2-(2-aminoethylamino)-2-methylethanol, 2-(2-aminoethylamino)-1-ethylethanol, 2-(2-aminoethylamino)-2-ethylethanol, 2-(2-aminoethylamino)-1,2-dimethylethanol, N-(2-hydroxyethyl)diethylene triamine, N-(2-hydroxyethyl)triethylene tetramine, N-(2 hydroxyethyl)tetraethylene pentamine, N-(2-hydroxyethyl)pentaethylene hexamine, N-(2-hydroxy-1-methylethyl)diethylene triamine, N-(2-hydroxy-2-methylethyl)diethylene triamine, N-(2-hydroxy-1-methylethyl)triethylene tetramine, N-(2-hydroxy-2-methylethyl)triethylene tetramine, N-(2-hydroxy-1-methylethyl)tetraethylene pentamine, N-(2-hydroxy-2-methylethyl)tetraethylene pentamine, N-(2-hydroxy-1-methylethyl)pentaethylene hexamine, N-(2-hydroxy-2-methylethyl)pentaethylene hexamine, N-(2-hydroxy-1-butyl)triethylene tetramine, N-(1-hydroxy-2-butyl)triethylene tetramine, N-(3-hydroxy-2-butyl)triethylene tetramine, N-

(2-hydroxy-1-butyl)tetraethylene pentamine, N-(1-hydroxy-2-butyl)tetraethylene pentamine, N-(3-hydroxy-2-butyl)tetraethylene pentamine, N-(2-hydroxyethyl)trimethylene diamine, N-(2-hydroxyethyl)tetramethylene diamine, N-(2-hydroxyethyl)pentamethylene diamine, N-(2-hydroxyethyl)hexamethylene diamine, N-(2-hydroxyethyl)tetraminoneopentane, N,N'-bis(2-hydroxyethyl)tetraaminoneopentane, N,N',N''-tris(2-hydroxyethyl)tetraaminoneopentane, N,N-di-(2-hydroxyethyl)ethylene diamine, N-(hydroxymethyl)ethylene diamine, N-(8-hydroxyoctyl)ethylene diamine, N-(8-hydroxy-2,7-dimethyloctyl)ethylene diamine, and the like.

The ratio of reactants utilized in the preparation of the compounds of this invention may be varied over a wide range. Generally, the reaction mixture will contain, for each equivalent (mole) of the acylating agent, at least about 0.5 equivalent, and in most cases at least about one equivalent, of the alkanol polyamine. In the practice of this invention, the equivalent weight of the alkanol polyamine is based on the number of primary amino groups per molecule. To illustrate, N-(2-hydroxyethyl)ethylene diamine has one equivalent per mole, and N,N'-bis(2-hydroxyethyl)tetraaminoneopentane has two equivalents per mole. Thus the former (monoamino) compounds will usually be employed in an approximately 1:1 mole ratio with the succinic acylating agent. In the case of the latter (diamino) compound, the mole ratio of the diamino compound to the succinic acylating agent will usually fall in the range of from about 1:1 to about 0.5:1 depending on the extent to which it is desired to acylate beyond one of the primary amino groups in the diamino compound.

The temperature of the reaction used to prepare the compounds of this invention is not critical, and generally, any temperature from room temperature up to the decomposition temperature of any of the reactants or the product can be utilized. Preferably, however, the temperature will be above about 50° C. and more generally from about 100° C. to about 250° C.

When preparing the dispersant-detergents of this invention, a mixture of one or more of the succinic acid-type acylating agents and one or more of the alkanol polyamines is heated optionally in the presence of a normally liquid, substantially inert organic liquid solvent/diluent. The reaction temperature will be, as defined above, generally above 50° C. up to the decomposition temperature of any of the reactants or of the product. The reaction of the acylating agent with the alkanol polyamine is accompanied by the formation of approximately one mole of water for each equivalent of the acid used. The removal of water formed may be effected conveniently by heating the product at a temperature above 100° C., preferably in the neighborhood of about 150° C. Removal of the water may be facilitated by blowing the reaction mixture with an inert gas such as nitrogen during heating. It may likewise be facilitated by the use of a solvent which forms an azeotrope with water. Such solvents are exemplified by benzene, toluene, naphtha, n-hexane, xylene, etc. The use of such solvents permits the removal of water at a lower temperature, e.g., 80° C.

The compounds of this invention are also useful as detergents for use in middle distillate (diesel) fuels to prevent or reduce deposits in fuel injectors, in fuel lines, and/or in related parts of the engine. Preferably the acyclic aliphatic substituent of the acylating agent for the detergents of these compression ignition engine fuel compositions is an alkyl or alkenyl group containing from 16 to 18 carbon atoms. Octadecenylsuccinic acid or anhydride is a particularly preferred acylating agent for making such detergents. Of the various hydroxyalkyl polyamines referred to hereinabove, 2-(2-aminoethylamino)ethanol is particularly preferred for making the detergents for diesel fuel usage.

Yet another aspect of this invention is a method for reducing deposits, especially carburetor and/or injector deposits, in an internal combustion engine, which method comprises: (i) blending with a major amount of a liquid hydrocarbon fuel a minor amount of a hydrocarbon-soluble detergent of this invention sufficient to reduce the formation of engine deposits, the detergent being prepared by reacting (a) at least one hydrocarbon-substituted succinic acid or acid derivative containing an average of from 16 to about 50 carbon atoms in the molecule and having an acyclic aliphatic group containing an average of at least 12 but less than 30 carbon atoms, with (b) at least one alkanol polyamine containing an average of at least 4 carbon atoms; and (ii) using the fuel composition in an internal combustion engine.

The following Examples illustrate the preparation of the dispersant-detergents of this invention. Unless otherwise indicated in the following examples and elsewhere in the specification and claims, all parts and percentages are by weight.

EXAMPLE 1

To a reactor equipped with a stirrer, a Dean-Stark trap and a condenser are added 159 parts of octadecenylsuccinic anhydride and 87 parts of xylene (mixed isomers). To this mixture are added 47 parts of 2-(2-aminoethylamino)ethanol and 52 parts of xylene. The resultant mixture is heated to reflux with stirring until all of the water formed in the reaction has been collected in the Dean-Stark trap (ordinarily in about 2.5 hours). The reaction mixture is indicated by infra-red to contain succinimide. The product is then stripped to 150° C. at 5 mm Hg vacuum. The residue is about 190 parts of predominantly $C_{18}$ alkenylsuccinimide of 2-(2-aminoethylamino)ethanol. Such product may be represented by the formula

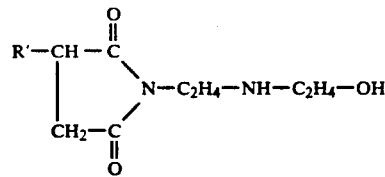

where R' is $C_{18}$ alkenyl.

EXAMPLE 2

Using the procedure and apparatus as described in Example 1 above, 116 parts of mixed $C_{16}$- and $C_{18}$-alkenylsuccinic anhydrides (average molecular weight of approximately 328) are reacted with 37.3 parts of 2-(2-aminoethylamino)ethanol in 130 parts of xylene. After the stripping operation, approximately 140 parts of product residue is recovered. This acylated product is predominantly a mixture of succinimides as depicted in Example 1 wherein R' is composed of $C_{16}$ and $C_{18}$ alkenyl groups.

EXAMPLE 3

To a reactor equipped as in Example 1 above are charged 56 parts of branched $C_{16}$-alkenylsuccinic anhydride (in which the alkenyl group is formed from dimerized 1-octene) and 52 parts of xylene. Then 16.8 parts of 2-(2-aminoethylamino)ethanol and 35 parts of xylene are charged into the reactor, and the resultant mixture is heated with stirring to reflux while azeotropically removing the water formed during the reaction. After collecting 3 parts of water (theory is about 2.8 parts) the product mixture is stripped at 35 mm Hg vacuum to 170° C. The residual acylated product (approximately 59 parts) is predominantly an alkenylsuccinimide of the formula

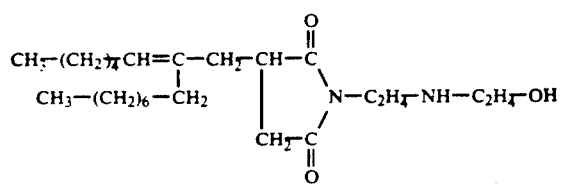

EXAMPLE 4

To a reactor equipped as in Example 1 above are charged 50 parts of branched $C_{20}$-alkenylsuccinic anhydride (in which the alkenyl group is formed from dimerized 1-decene) and 35 parts of xylene. Then 14.3 parts of 2-(2-aminoethylamino)ethanol and 52 parts of xylene are charged into the reactor, and the resultant mixture is heated with stirring to reflux while azeotropically removing the water formed during the reaction. After collecting about 2.5 parts of water (theory is about 2.4 parts) the product mixture is stripped at 35 mm Hg vacuum to 170° C. The residual acylated product (approximately 59.9 parts) is predominantly an alkenylsuccinimide of the formula

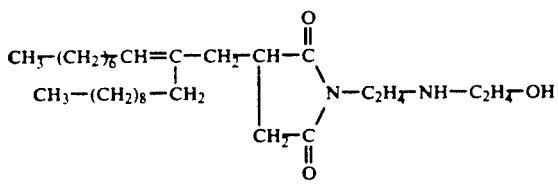

EXAMPLE 5

The procedure of Example 3 above is repeated using 50 parts of a mixture of $C_{16}$-, $C_{18}$-, $C_{20}$-, $C_{22}$-, $C_{24}$-, and $C_{26}$-alkenylsuccinic anhydrides and 15.5 parts of 2-(2-aminoethylamino)ethanol in 87 parts of refluxing xylene. The olefin mixture from which this alkenyl succinic anhydride reactant is made is composed, on a weight basis, of 0.8% $C_{16}H_{32}$, 8.2% $C_{18}H_{36}$, 42.2% $C_{20}H_{40}$, 33.3% $C_{22}H_{44}$, 14.7% $C_{24}H_{48}$ and 0.8% $C_{26}H_{52}$. After stripping the reaction mixture, a product composed predominantly of a mixture of $C_{16-26}$-alkenylsuccinimides of 2-(2-aminoethylamino)ethanol is recovered. The alkenyl groups of this succinimide product are in proportions averaging in the range of from between about $C_{20}$ to about $C_{22}$.

EXAMPLE 6

Using the general procedure of Example 1 above, a mixture of $C_{22}$- and $C_{24}$-alkenylsuccinic anhydrides with an average molecular weight of 440 and 2-(2-aminoethylamino)ethanol in equimolar quantities are reacted in refluxing xylene with removal of by-product water. The product remaining after the stripping operation is predominantly an acylated compound as depicted in Example 1 above wherein R' is docosenyl ($C_{22}$) and tetracosenyl ($C_{24}$).

EXAMPLE 7

By use of the procedure of Example 1 above, 50 parts of a $C_{18}$ alkenyl-substituted succinic anhydride is reacted with 33 parts of N-(2-hydroxy-1-methylethyl)tetraethylene pentamine in 100 parts of refluxing xylene. The product remaining after the stripping operation is predominantly a $C_{18}$ alkenylsuccinimide of N-(2-hydroxy-1-methylethyl)tetraethylene pentamine.

EXAMPLE 8

The procedure of Example 1 above is repeated using 50 parts of a $C_{12}$ alkenyl-substituted succinic anhydride and 48 parts of an equimolar mixture of N-(2-hydroxyethyl)diethylene triamine and N-(2-hydroxyethyl)triethylene tetramine in 100 parts of refluxing xylene. After stripping, a product composed predominantly of a mixture of $C_{12}$ alkenylsuccinimides of N-(2-hydroxyethyl)diethylene triamine and N-(2-hydroxyethyl)triethylene tetramine is recovered.

EXAMPLE 9

Repetition of the procedure of Example 1 above is done using 159 parts of a $C_{18}$ alkenyl-substituted succinic anhydride and 73 parts of N-(2-hydroxyethyl)hexamethylene diamine in 150 parts of refluxing xylene. After stripping, a product composed predominantly of $C_{18}$ alkenylsuccinimide of N-(2-hydroxyethyl)hexamethylene diamine is recovered.

EXAMPLE 10

Using the same general procedure as in Example 1, N,N'-bis(2-hydroxyethyl) tetraaminoneopentane is reacted with a $C_{28}$ alkenylsuccinic anhydride in refluxing xylene. In one case the reactants are used in a 1.1:1 mole ratio (anhydride:aminoneopentane). In another case the reactants are employed in a ratio of 1.5 miles of the anhydride per moles of the aminoneopentane reactant. In still another case the ratio of the anhydride to the aminoneopentane reactant is 2:1. Succinimides with increasing proportions of bis substitution are formed in these respective cases.

EXAMPLE 11

Hydrogenations at 60°-70° C. and about 30 psi hydrogen pressure using palladium on charcoal as catalyst are conducted on products made as in Examples 1-10 above yielding corresponding alkyl-substituted succinimide products.

EXAMPLE 12

By use of the general procedure set forth in Example 1, the following compounds are prepared from the alkenyl succinic anhydride in which the alkenyl group is a substantially straight chain alkenyl group of the appropriate specified chain length:

$C_{28}$ alkenylsuccinimide of 2-(2-aminoethylamino)ethanol $C_{26}$ alkenylsuccinimide of 2-(2-aminoethylamino)ethanol $C_{24}$ alkenylsuccinimide of 2-(2-aminoethylamino)ethanol
$C_{22}$ alkenylsuccinimide of 2-(2-aminoethylamino)ethanol
$C_{20}$ alkenylsuccinimide of 2-(2-aminoethylamino)ethanol
$C_{18}$ alkenylsuccinimide of 2-(2-aminoethylamino)ethanol
$C_{16}$ alkenylsuccinimide of 2-(2-aminoethylamino)ethanol
$C_{14}$ alkenylsuccinimide of 2-(2-aminoethylamino)ethanol
$C_{12}$ alkenylsuccinimide of 2-(2-aminoethylamino)ethanol

EXAMPLE 13

By use of the general procedure set forth in Example 1, the following compounds are prepared from an alkyl-substituted succinic anhydride in which the alkyl group is a substantially straight chain alkyl group of the appropriate specified chain length:

$C_{28}$ alkylsuccinimide of 2-(2-aminoethylamino)ethanol
$C_{26}$ alkylsuccinimide of 2-(2-aminoethylamino)ethanol
$C_{24}$ alkylsuccinimide of 2-(2-aminoethylamino)ethanol
$C_{22}$ alkylsuccinimide of 2-(2-aminoethylamino)ethanol
$C_{20}$ alkylsuccinimide of 2-(2-aminoethylamino)ethanol
$C_{18}$ alkylsuccinimide of 2-(2-aminoethylamino)ethanol
$C_{16}$ alkylsuccinimide of 2-(2-aminoethylamino)ethanol
$C_{14}$ alkylsuccinimide of 2-(2-aminoethylamino)ethanol
$C_{12}$ alkylsuccinimide of 2-(2-aminoethylamino)ethanol

EXAMPLE 14

By use of the general procedure set forth in Example 3, the following compounds are prepared from an alkenyl succinic anhydride in which the alkenyl group contains the appropriate number of carbon atoms and is branched on its beta carbon atom into two branches, one of which contains two less carbon atoms than the other:

$C_{28}$ alkenylsuccinimide of 2-(2-aminoethylamino)ethanol
$C_{26}$ alkenylsuccinimide of 2-(2-aminoethylamino)ethanol
$C_{24}$ alkenylsuccinimide of 2-(2-aminoethylamino)ethanol
$C_{22}$ alkenylsuccinimide of 2-(2-aminoethylamino)ethanol
$C_{20}$ alkenylsuccinimide of 2-(2-aminoethylamino)ethanol
$C_{18}$ alkenylsuccinimide of 2-(2-aminoethylamino)ethanol
$C_{16}$ alkenylsuccinimide of 2-(2-aminoethylamino)ethanol
$C_{14}$ alkenylsuccinimide of 2-(2-aminoethylamino)ethanol
$C_{12}$ alkenylsuccinimide of 2-(2-aminoethylamino)ethanol

EXAMPLE 15

By use of the general procedure set forth in Example 3, the following compounds are prepared from an alkyl-substituted succinic anhydride in which the alkyl group contains the appropriate number of carbon atoms and is branched on its beta carbon atom into two branches, one of which contains two less carbon atoms than the other:

$C_{28}$ alkylsuccinimide of 2-(2-aminoethylamino)ethanol
$C_{26}$ alkylsuccinimide of 2-(2-aminoethylamino)ethanol
$C_{24}$ alkylsuccinimide of 2-(2-aminoethylamino)ethanol
$C_{22}$ alkylsuccinimide of 2-(2-aminoethylamino)ethanol
$C_{20}$ alkylsuccinimide of 2-(2-aminoethylamino)ethanol
$C_{18}$ alkylsuccinimide of 2-(2-aminoethylamino)ethanol
$C_{16}$ alkylsuccinimide of 2-(2-aminoethylamino)ethanol
$C_{14}$ alkylsuccinimide of 2-(2-aminoethylamino)ethanol
$C_{12}$ alkylsuccinimide of 2-(2-aminoethylamino)ethanol The effectiveness of the compounds of this invention in reducing carburetor deposits was demonstrated by a series of standard CRC carburetor tests. On completion of each such engine test the weight of deposits formed on the carburetor sleeve during the test was measured. Thus the lower the weight, the more effective was the fuel composition. The same base fuel was used in each series of tests, and the additives employed therein and results obtained are summarized in Tables I–III below. All additive concentrations are expressed therein as pounds per thousand barrels (ptb). Baseline runs were conducted before and after the runs on the fuels of this invention and the values shown in the tables are the averages of such before and after runs.

TABLE I

| Additive | Additive Conc., ptb | Sleeve Wt., mg | % Reduction |
|---|---|---|---|
| None | — | 27.2 | — |
| Ex. 1 | 10 | 1.8 | 93.4 |
| Ex. 2 | 10 | 9.4 | 65.4 |

TABLE II

| Additive | Additive Conc., ptb | Sleeve Wt., mg | % Reduction |
|---|---|---|---|
| None | — | 23.9 | — |
| Ex. 1 | 5 | 9.4 | 60.7 |
| Ex. 2 | 5 | 12.7 | 46.9 |

TABLE III

| Additive | Additive Conc., ptb | Sleeve Wt., mg | % Reduction |
|---|---|---|---|
| None | — | 22.5 | — |
| Ex. 1 | 10 | 2.0 | 91.1 |
| Ex. 3 | 10 | 3.7 | 83.6 |
| Ex. 4 | 10 | 2.7 | 88.0 |
| Ex. 5 | 10 | 3.4 | 84.9 |
| Ex. 6 | 10 | 5.1 | 77.3 |

The amount of the detergent of this invention included in the fuel compositions may vary over a wide range although it is preferred not to include unnecessarily large excesses of the detergent. The amount included in the fuel should be an amount sufficient to improve the desired properties such as the prevention and/or reduction in the amount of deposits on the various parts of internal combustion engines such as in the carburetor and the fuel injector nozzles when the fuel is used to operate internal combustion engines. The fuel may contain from about 1 to about 10,000, and preferably from about 5 to about 5000 parts per million parts by weight of the fuel. The detergents of this invention utilized in the fuel compositions are hydrocarbon-soluble in the sense that the detergents are at least sufficiently soluble in the hydrocarbon fuel being employed to provide a solution containing the desired concentrations specified above.

The fuel compositions can be prepared by adding the detergents of this invention to a liquid hydrocarbon fuel, or a concentrate of the detergent in a substantially inert, normally liquid organic solvent/diluent such as mineral oil, xylene, or a normally liquid fuel as described above can be prepared, and the concentrate added to the liquid hydrocarbon fuel. The concentrates generally contain about 5-95, usually 10-90% of the detergent of the invention, and the concentrate can also contain any of the conventional additives for fuels such as those described below.

In addition to the detergent of this invention, other conventional fuel additives can be employed in the fuel compositions and concentrates provided by the present invention. Thus, the fuels can contain antiknock agents such as tetraalkyllead compounds, organomanganese additives such as methylcyclopentadienylmanganese tricarbonyl, lead scavengers such as haloalkanes (e.g., ethylene dichloride and ethylene dibromide), deposit preventors or modifiers such as trialkyl or triaryl phosphates, dyes, antioxidants such as 2,6-di-tert-butyl-4-methyl phenol, rust-inhibitors, such as alkylated succinic acids and anhydrides, gum inhibitors, metal deactivators, demulsifiers, upper cylinder lubricants, anti-icing agents, etc. The middle distillate or diesel fuels may contain ignition accelerators such as alkyl nitrates, combustion improvers such as methylcyclopentadienyl-manganese tricarbonyl, alcohols, corrosion inhibitors, antioxidants, stabilizers, particulate reducing additives, and the like.

This invention is susceptible to considerable variation in its practice within the spirit and scope of the ensuing claims, the embodiments described hereinbefore being illustrative, but not limitative, of its practice.

What is claimed is:

1. A hydrocarbon-soluble succinimide prepared by reacting
    a) at least one substituted succinic acid or acid derivative thereof containing an average of from 16 to about 50 carbon atoms in the molecule and having an acyclic aliphatic substitutent group containing an average of at least 12 but less than 30 carbon atoms, said substituent group being bifurcated on its beta carbon atom into two branches, one of which contains at least 4 carbon atoms and the other of which contains at least 6 carbon atoms, with
    b) at least one alkanol polyamine containing an average of at least 4 carbon atoms and containing at least one primary amino group.

2. A substituted succinimide represented by the formula $$\begin{array}{c} \text{R}'-\text{CH}-\overset{\overset{\text{O}}{\|}}{\text{C}} \\ | \qquad\qquad \diagdown \\ \qquad\qquad\qquad\qquad \text{N}-\text{C}_2\text{H}_4-\text{NH}-\text{C}_2\text{H}_4-\text{OH} \\ | \qquad\qquad \diagup \\ \text{CH}_2-\underset{\underset{\text{O}}{\|}}{\text{C}} \end{array}$$

where R' is a substantially straight chain alkyl or alkenyl group containing an average of at least 14 but no more than about 2 carbon atoms.

3. A substituted succinimide as claimed in claim 2 wherein the alkyl or alkenyl group contains an average of at least 16 but not more than about 26 carbon atoms.

4. A substituted succinimide as claimed in claim 2 wherein the alkyl or alkenyl group contains an average of about 26 carbon atoms.

5. A substituted succinimide as claimed in claim 2 wherein the alkyl or alkenyl group contains an average of about 24 carbon atoms.

6. A substituted succinimide as claimed in claim 2 wherein the alkyl or alkenyl group contains an average of about 22 carbon atoms.

7. A substituted succinimide as claimed in claim 2 wherein the alkyl or alkenyl group contains an average of about 20 carbon atoms.

8. A substituted succinimide as claimed in claim 2 wherein the alkyl or alkenyl group contains an average of about 18 carbon atoms.

9. A substituted succinimide as claimed in claim 2 wherein the alkyl or alkenyl group contains an average of about 16 carbon atoms.

10. A substituted succinimide as claimed in claim 2 represented by the formula $$\begin{array}{c} \text{R}'-\text{CH}-\overset{\overset{\text{O}}{\|}}{\text{C}} \\ | \qquad\qquad \diagdown \\ \qquad\qquad\qquad\qquad \text{N}-\text{C}_2\text{H}_4-\text{NH}-\text{C}_2\text{H}_4-\text{OH} \\ | \qquad\qquad \diagup \\ \text{CH}_2-\underset{\underset{\text{O}}{\|}}{\text{C}} \end{array}$$

where R' is $C_{18}$ alkenyl.

11. A substituted succinimide as claimed in claim 2 represented by the formula $$\begin{array}{c} \text{R}'-\text{CH}-\overset{\overset{\text{O}}{\|}}{\text{C}} \\ | \qquad\qquad \diagdown \\ \qquad\qquad\qquad\qquad \text{N}-\text{C}_2\text{H}_4-\text{NH}-\text{C}_2\text{H}_4-\text{OH} \\ | \qquad\qquad \diagup \\ \text{CH}_2-\underset{\underset{\text{O}}{\|}}{\text{C}} \end{array}$$

where R' is a mixture of hexadecenyl, octadecenyl, eicosenyl, docosenyl, tetracosenyl, and hexacosenyl groups in proportions averaging from about $C_{20}$ to about $C_{22}$.

12. A succinimide as claimed in claim 1 wherein the substituted succinic acid or acid derivative thereof is predominantly or entirely an alkenylsuccinic acid or anhydride in which the alkenyl group has the formula $$CH_3-(CH_2)_n-CH=C-CH_2- \\ | \\ CH_3-(CH_2)_{n+2}-CH_2$$

where n is an integer in the range of 2 to 10.

13. A succinimide as claimed in claim 1 wherein the succinic acid or acid derivative is predominantly or entirely an alkenylsuccinic acid or anhydride in which the alkenyl group has the formula $$CH_3-(CH_2)_6-CH=C-CH_2- \\ | \\ CH_3-(CH_2)_8-CH_2$$

14. A succinimide as claimed in claim 1 wherein the substituted succinic acid or acid derivative is predominantly or entirely an alkenylsuccinic acid or anhydride in which the alkenyl group has the formula $$CH_3-(CH_2)_4-CH=C-CH_2-$$
$$\phantom{CH_3-(CH_2)_4-CH=C}|$$
$$\phantom{CH_3-(CH_2)_4-C}CH_3-(CH_2)_6-CH_2$$

15. A succinimide as claimed in claim 1 wherein the substituent group contains an average of 30 carbon atoms.

16. A succinimide as claimed in claim 1 wherein the substituent group contains an average of about 28 carbon atoms.

17. A succinimide as claimed in claim 1 wherein the substituent group contains an average of about 26 carbon atoms.

18. A succinimide as claimed in claim 1 wherein the substituent group contains an average of about 24 carbon atoms.

19. A succinimide as claimed in claim 1 wherein the substituent group contains an average of about 22 carbon atoms.

20. A succinimide as claimed in claim 1 wherein the substituent group contains an average of about 20 carbon atoms.

21. A succinimide as claimed in claim 1 wherein the substituent group contains an average of about 18 carbon atoms.

22. A succinimide as claimed in claim 1 wherein the substituent group contains an average of about 16 carbon atoms.

23. A succinimide as claimed in claim 1 wherein the alkanol polyamine contains only one primary amino group in the molecule.

24. A succinimide as claimed in claim 1 wherein the alkanol polyamine contains an average of more than one primary amino group in the molecule.

25. A succinimide as claimed in claim 24 having an average of more than one succinimide group per molecule.

26. A succinimide as claimed in claim 1 wherein the alkanol polyamine contains an average of at least two primary amino groups in the molecule.

27. A substituted succinimide represented by the formula $$R'-CH-\underset{\underset{O}{\|}}{C}\diagdown$$
$$\phantom{R'-CH}|\phantom{CCCC}N-C_2H_4-NH-C_2H_4-OH$$
$$\phantom{R'-C}CH_2-\underset{\underset{O}{\|}}{C}\diagup$$

where R' is an alkyl or alkenyl group bifurcated on its beta carbon atom into two branches, one of which contains at least 4 carbon atoms and the other of which contains at least 6 carbon atoms, such alkyl or alkenyl group containing an average of at least 12 but less than 30 carbon atoms.

28. A succinimide as claimed in claim 27 wherein R' contains about 28 carbon atoms.

29. A succinimide as claimed in claim 27 wherein R' contains about 26 carbon atoms.

30. A succinimide as claimed in claim 27 wherein R' contains about 24 carbon atoms.

31. A succinimide as claimed in claim 27 wherein R' contains about 22 carbon atoms.

32. A succinimide as claimed in claim 27 wherein R' contains about 20 carbon atoms.

33. A succinimide as claimed in claim 27 wherein R' contains about 18 carbon atoms.

34. A succinimide as claimed in claim 27 wherein R' contains about 16 carbon atoms.

35. A succinimide as claimed in claim 27 wherein R' contains about 14 carbon atoms.

* * * * *

UNITED STATES PATENT AND TRADEMARK OFFICE
CERTIFICATE OF CORRECTION

PATENT NO. : 5,122,616
DATED : JUNE 16, 1992
INVENTOR(S) : DENNIS J. MALFER

It is certified that error appears in the above-identified patent and that said Letters Patent is hereby corrected as shown below:

Col. 15, Line 59, change "2" to -- 28 --.

Col. 16, Line 54, after "the" insert -- substituted --.

Signed and Sealed this

Seventeenth Day of August, 1993

Attest:

BRUCE LEHMAN

Attesting Officer

Commissioner of Patents and Trademarks